United States Patent [19]

Francke

[11] Patent Number: 4,853,217

[45] Date of Patent: Aug. 1, 1989

[54] **METHODS AND COMPOSITIONS FOR CONTROLLING THE PEAR LEAF BLISTER MOTH, *LEUCOPTERA SCITELLA***

[75] Inventor: Wittko Francke, Reinbek, Fed. Rep. of Germany

[73] Assignee: Toyo Seikan Kaisha, Ltd., Tokyo, Japan

[21] Appl. No.: 45,453

[22] Filed: May 4, 1987

[30] Foreign Application Priority Data

May 10, 1986 [DE] Fed. Rep. of Germany ....... 3615854

[51] Int. Cl.$^4$ .............................................. A61K 31/74

[52] U.S. Cl. ..................................... 424/84; 514/789; 585/16

[58] Field of Search ........................... 585/16; 424/84; 514/789

[56] References Cited

PUBLICATIONS

Chemical Abstracts, 106: 193131g (1987).

*Primary Examiner*—Curtis R. Davis
*Attorney, Agent, or Firm*—Sherman and Shalloway

[57] ABSTRACT

5,9-dimethylheptadecane is used an an attractant in a composition for controlling the pear leaf blister moth, *Leucoptera scitella*.

7 Claims, No Drawings

METHODS AND COMPOSITIONS FOR CONTROLLING THE PEAR LEAF BLISTER MOTH, LEUCOPTERA SCITELLA

The pear leaf blister moth, Leucoptera (Cemiostoma) scitella (Zell.) from the Lyonetiidae family causes damage to various fruit trees.

This small moth appears sporadically in European fruit cultivation regions, but substantial damage, especially to apple orchards, is reported particularly from France, Italy and Hungary (cf. HEINZE, 1978: Schädlinge und Krankheiten im Obst- und Weinbau, page 165; Celli 1975, 1984: Instituto di Entomologia, Universita di Bologna, Italy; CHAMBON 1981: Phytoma 331, 18–20 (France); Dulic, Injac, 1981: Zastita Bilja 32, 409–426 (Yugoslavia); and Balazas 1983: Novenyvedelem 19, 305–306 (Hungary).

The economic significance of the pest is that larger or smaller parts of the leaf surface are destroyed and are not available for assimilation. In the event of severe attack, the leaves may be dropped prematurely, and premature ripening of the fruit may result. Leaf fall prevents the incorporation of sufficient reserve substances for the winter.

Because they keep themselves concealed, the pear leaf blister moths are not easy to control. Insecticidal active ingredients from the group consisting of the phosphates, which have an intense effect, can be used. However, all products of this type have the disadvantage that they do not have a selective action and in many cases are also toxic to warm-blooded animals.

No reliable method for detecting the presence of this harmful moth or selective method of control is known to date, and selective control is therefore impossible.

It is known per se that, in the case of moths, female animals ready to mate produce sexual attractants (pheromones) and excrete them into the environment; male moths of the same species can then find the females with the aid of this scent.

In principle, there are three different possibilities for using sexual attractants in crop protection.

Pheromone traps charged with synthetic sexual attractant lures are suspended in potential areas of attack. The male moths caught in the trap provide evidence of the presence of the pest. Moreover, it is possible to obtain information about the severity of infestation and the correct time for control.

The attractant can be combined with insecticidal active ingredients. It is possible to add insecticides to the lure or the trap, or just to treat the immediate environment of the trap, so that the majority of the male moth population attracted from remote distances are killed (trapping technique). Pollution of the biotope is reduced to an acceptable level.

Finally, the pest can be controlled by the method in which the air space is saturated with sexual attractants or substances having a similar action. The male moths are disturbed in their search for the females, and mating of the animals is thus prevented. In this case, a fairly large amount of the attractant is distributed uniformly in the air space in the entire area of the crop to be protected, so that the males can perceive the presence of the scent everywhere and their normal orientation behavior is disturbed.

Even in this last-mentioned method of using sexual attractants, only relatively small amounts of the active ingredients are required, often only fractions of the usual doses of the traditional insecticidal active ingredients (Birch (ed.): Pheromones, North Holland Publ. Co., 1974).

This is an extremely selective, nontoxic method of control, with the greatest possible protection of nontarget organisms, in particular useful animals.

We have found that formulations which contain 5,9-dimethylheptadecane(I) constitute an effective attractant for use on Leucoptera scitella.

The present invention therefore relates to compositions for attracting or confusing male animals of the Leucoptera scitella species, which contain a compound I.

A possible synthesis route for 5,9-dimethylheptadecane is that described in the Preparation Example below.

PREPARATION EXAMPLE

Cf. Scheme Below

An ether solution of the Grignard compound obtained from n-chlorooctane is added dropwise, under nitrogen, to a solution of ethyl levulate in ether, cooled to 0° C. The resulting lactone, 5-methyl-5-octyltetrahydrofuran-2-one (II), is converted with methanolic hydrochloric acid to methyl 4-chloro-4-methyldodecanoate (III), which, after eliminating hydrochloric acid by heating and then carrying out hydrogenation, gives racemic methyl 4-methyldodecanoate (IV), from which 4-methyldodecanoic acid (V) is obtained by hydrolysis. At the same time, the tosylate is prepared from 2-hexanol and, when reacted with sodium malonate in ethanolic solution, forms ethyl 2-carbethoxy-3-methylheptanoate (VI). This is converted to racemic 3-methylheptanoic acid (VII) by hydrolysis and thermal decarboxylation.

The pheromone, 5,9-dimethylheptadecane, is prepared from 4-methyldodecanoic acid (V) and 3-methylheptanoic acid (VII) by Kolbe electrolysis. 3 g of (V) and 2 g of (VII) are dissolved in 50 ml of methanol, and the solution is neutralized with trimethylamine. Electrolysis is then carried out for 2 hours at room temperature and at a current density of 0.3 amp/cm$^2$ using Pt electrodes. The methanol is removed under reduced pressure, the residue is taken up in ether, and the solution is washed in succession with HCL, NaOH and H$_2$O and dried with MgSO$_4$. After removal of the ether, the product is distilled under reduced pressure.

Bp. 83°C./0.8 mm Hg; Yield 30%.

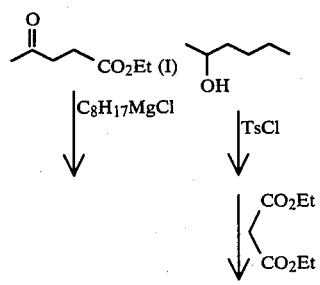

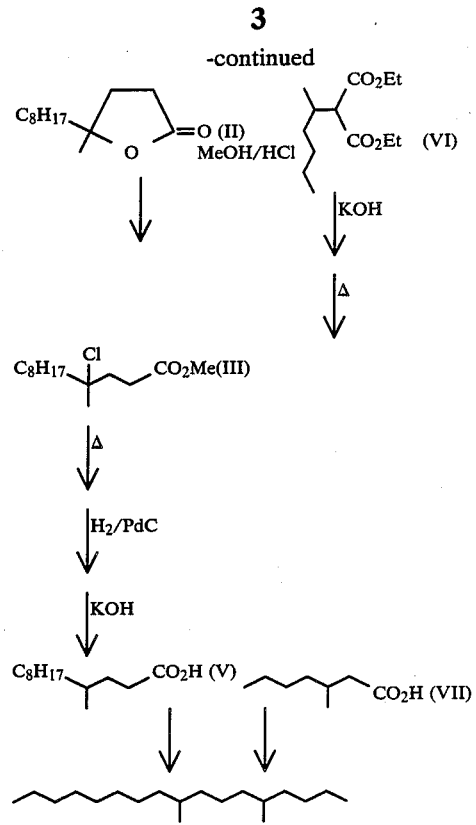

The active ingredient can be formulated according to the invention in the form of both liquid and solid preparations.

Suitable solvents are high boiling, aromatic, aliphatic or cycloaliphatic compounds. In addition to hydrocarbons, esters, ethers or ketones are particularly suitable. Typical examples of members of these classes are xylene, methylnaphthalenes, liquid paraffins, cyclohexanone, ethylglycol acetate, isophorone and dibutyl phthalate.

To extend the period of action, solutions in vegetable, animal or synthetic oils or fats and other evaporation-inhibiting solvents having a low vapor pressure (eg. dioctyl phthalate) can be prepared.

Solid formulations are obtained by binding the active ingredient in or to natural or synthetic solid carriers, such as rubber, cork, cellulose, plastics, ground coal, wood dust, silicates, pumice, calcined clay or similar solid carriers. Active ingredient enclosed in plastic capsules or containers or in multilayer plastic flakes can diffuse through the walls; this too results in uniform release to the air over prolonged periods. Furthermore, the active ingredient can be evaporated from suitable containers (capillaries or other vessels) through narrow openings, with the result that particularly constant scent concentrations are achieved over prolonged periods.

The content of active ingredient in these formulations can vary within wide limits. In general, the ratio of active ingredient to additive may be, for example, from 10:1 to 1:10$^3$. In formulations in capsules or other suitable containers, for example, the active ingredient can be used in pure, undiluted form and may be present in a very large amount of up to 90% by weight, based on the total formulation. In general, however, very low concentrations of active ingredient in the formulations are sufficient to have the desired effect on Leucoptera males. A ratio of active ingredient to additive of from 1:3 to 1:10$^2$ is preferred.

The active ingredient can also be applied in comparatively high concentrations so that, through disorientation and confusion, the males are hindered not only in their search for the females but also directly in mating. Formulations which are most suitable for this method are those containing sparingly volatile additives which release the active ingredient over a protracted period, eg. rubber, pulp, waxes, polymers or evaporation-inhibiting liquid paraffins, as well as formulations in capsules or other containers (capillaries) which release the attractant either through their wall or through narrow openings. The concentration of active ingredient in this case is in general from 10:1 to 1:10$^3$.

Field trials in a potential area of infestation by Leucoptera scitella have confirmed the biological function of the claimed pheromone component.

For this purpose, rubber carriers were impregnated with the stated scent and placed in delta-type traps having an adhesive surface. Evaluation was carried out after fixed time intervals by counting the Leucoptera males caught in the pheromone traps. The experiments were carried out in Hungary in 1985, with several replications.

TABLE 1

| Lure charge | Number of male L. scitella moths caught | | | |
|---|---|---|---|---|
| μg | Trap 1 | 2 | 3 | Total |
| 1000 | 147 | 86 | 98 | 331 |
| 100 | 23 | 31 | 21 | 75 |
| 10 | 5 | 0 | 28 | 33 |
| 1 | 0 | 1 | 9 | 10 |

I claim:

1. A composition for controlling the pear leaf blister moth, Leucoptera scitella, which comprises: an effective amount of 5,9-dimethylheptadecane as an active agent for attracting the moths and a carrier or diluent for the active agent.

2. A composition for controlling the pear leaf blisher moth, *Leucoptera scitella*, which comprises: an effective amount of 5,9-dimethylheptadecane as a moth attracting agent and a high boiling solvent for said agent.

3. A composition for controlling the pear leaf blister moth, *Leucoptera scitella*, which comprises: an effective amount of 5,9-dimethylheptadecane as a moth attracting agent and a solid carrier for said agent.

4. A composition as defined in claim 1, which composition further contains an effective amount of an insecticide which is toxic to said moths.

5. A method for determining the presence of the pear leaf blister moth in a given area, which comprises: placing an effective amount of a composition as defined in claim 1 in a moth trap and thereafter measuring the severity of infestation of the moths in the area.

6. A method for controlling the pear leaf blister moth which comprises: applying to a moth trap in an area to be freed of infestation an effective amount of a composition as defined in claim 1 to attract said moths and an effective amount of an insecticide which is toxic to said moths.

7. A method for influencing the reproduction rate of the pear leaf blister moth which comprises:
saturating the air space in the area to be protected with the composition defined in claim 1, whereby the male moths are disturbed in their search for females and thus mating of the animals is prevented.

* * * * *

UNITED STATES PATENT AND TRADEMARK OFFICE
CERTIFICATE OF CORRECTION

PATENT NO. : 4,853,217

DATED : August 1, 1989

INVENTOR(S) : Wittko FRANCKE

It is certified that error appears in the above-identified patent and that said Letters Patent is hereby corrected as shown below:

On the title page assignee should read

-- BASF Aktiengesellschaft,
Ludwigshafen, Federal Republic of Germany --

ATTORNEY, AGENT, or FIRM

-- KEIL & WEINKAUF --

Signed and Sealed this

Nineteenth Day of June, 1990

Attest:

HARRY F. MANBECK, JR.

*Attesting Officer*     *Commissioner of Patents and Trademarks*